US012611269B2

(12) United States Patent
Ciriello et al.

(10) Patent No.: US 12,611,269 B2
(45) Date of Patent: Apr. 28, 2026

(54) ROBOTIC DENTAL SYSTEM AND METHOD OF PREPARING FOR A ROBOTIC DENTAL PROCEDURE

(71) Applicant: Perceptive Technologies, Inc., Boston, MA (US)

(72) Inventors: Christopher John Ciriello, Boston, MA (US); Phillip Getto, Wellesley, MA (US); James Patrick Jackson, Victoria (CA); Nathan John Müller, Victoria (CA)

(73) Assignee: Perceptive Technologies, Inc., Boston, MA (US)

( * ) Notice: Subject to any disclaimer, the term of this patent is extended or adjusted under 35 U.S.C. 154(b) by 0 days.

(21) Appl. No.: 18/768,553

(22) Filed: Jul. 10, 2024

(65) Prior Publication Data

US 2024/0366321 A1 Nov. 7, 2024

Related U.S. Application Data

(63) Continuation of application No. 18/656,502, filed on May 6, 2024.

(Continued)

(51) Int. Cl.
| | |
|---|---|
| *A61B 34/30* | (2016.01) |
| *A61C 7/08* | (2006.01) |

(52) U.S. Cl.
CPC .............. *A61B 34/30* (2016.02); *A61C 7/08* (2013.01); *A61B 2034/305* (2016.02)

(58) Field of Classification Search
CPC ...... A61B 34/30; A61B 2034/301–305; A61C 7/08
See application file for complete search history.

(56) References Cited

U.S. PATENT DOCUMENTS

| | | | |
|---|---|---|---|
| 3,772,790 A | 11/1973 | Swan-Gett et al. | |
| 4,941,826 A | 7/1990 | Loran et al. | |

(Continued)

FOREIGN PATENT DOCUMENTS

| | | |
|---|---|---|
| CN | 101883536 A | 11/2010 |
| CN | 105832419 A | 8/2016 |

(Continued)

OTHER PUBLICATIONS

European Patent Office, European Search Report in re European Patent Application No. 18757107.0, 21 pp. 2021-02-12.

(Continued)

*Primary Examiner* — Yogesh P Patel
(74) *Attorney, Agent, or Firm* — George Jakobsche Patent Counsel PLLC

(57) ABSTRACT

A dental robot includes a platform and a suspension system. The suspension system supports the platform and automatically compensates for weights of the platform and a robot arm, end effector, and tooth clamp attached to the platform. The suspension system maintains a constant height of the platform above a base, absent an external force on the tooth clamp. The suspension system allows position and orientation of the platform to change, relative to the base, in response to an external force on the tooth clamp greater than about 0.1 N, such as a result of movement (change in position and/or orientation) of a subject. Consequently, the position and orientation of the platform remain fixed, relative to the subject's teeth, in response to movement of the teeth.

15 Claims, 13 Drawing Sheets

Related U.S. Application Data

(60) Provisional application No. 63/500,268, filed on May 4, 2023.

(56) References Cited

U.S. PATENT DOCUMENTS

| | | | |
|---|---|---|---|
| 5,122,060 | A | 6/1992 | Vassiliadis et al. |
| 5,343,391 | A | 8/1994 | Mushabac |
| 5,516,286 | A | 5/1996 | Kushner |
| 6,049,743 | A | 4/2000 | Baba |
| 6,518,033 | B1 | 2/2003 | Gromeier et al. |
| 6,802,713 | B1 | 10/2004 | Chishti et al. |
| 8,251,984 | B2 | 8/2012 | Monty |
| 8,416,984 | B2 | 4/2013 | Liang et al. |
| 8,716,973 | B1 | 5/2014 | Lammertse |
| 9,408,673 | B2 | 8/2016 | Monty |
| 9,554,872 | B2 | 1/2017 | Koubi et al. |
| 9,622,833 | B2 | 4/2017 | Monty |
| 9,675,419 | B2 | 6/2017 | Akeel et al. |
| 9,788,915 | B2 | 10/2017 | Monty et al. |
| 10,016,242 | B2 | 7/2018 | Salcedo et al. |
| 10,052,171 | B1 | 8/2018 | Almalki |
| 11,864,727 | B2 * | 1/2024 | Ciriello ................ A61B 90/361 |
| 2002/0133095 | A1 | 9/2002 | Mushabac |
| 2005/0084816 | A1 | 4/2005 | Mehdizadeh |
| 2005/0193451 | A1 | 9/2005 | Quistgaard et al. |
| 2006/0127848 | A1 | 6/2006 | Sogo et al. |
| 2006/0177796 | A9 | 8/2006 | Heasley et al. |
| 2007/0265495 | A1 | 11/2007 | Vayser |
| 2008/0009697 | A1 | 1/2008 | Haider et al. |
| 2008/0153067 | A1 | 6/2008 | Berckmans et al. |
| 2009/0186318 | A1 | 7/2009 | Assa et al. |
| 2009/0248184 | A1 | 10/2009 | Steingart et al. |
| 2010/0105011 | A1 | 4/2010 | Karkar et al. |
| 2011/0143306 | A1 | 6/2011 | Hirsch et al. |
| 2012/0059378 | A1 | 3/2012 | Farrell |
| 2012/0231421 | A1 | 9/2012 | Boerjes et al. |
| 2013/0211242 | A1 | 8/2013 | Bertrand et al. |
| 2013/0322719 | A1 | 12/2013 | Dekel et al. |
| 2014/0272789 | A1 | 9/2014 | Mozes et al. |
| 2015/0057576 | A1 | 2/2015 | Chen |
| 2015/0057675 | A1 | 2/2015 | Akeel et al. |
| 2015/0320320 | A1 | 11/2015 | Kopelman et al. |
| 2016/0135816 | A1 | 5/2016 | Lavallee et al. |
| 2016/0338803 | A1 | 11/2016 | Pesach |
| 2016/0354169 | A1 | 12/2016 | Suttin et al. |
| 2016/0367336 | A1 | 12/2016 | Lv et al. |
| 2016/0367343 | A1 | 12/2016 | Mozes et al. |
| 2017/0079746 | A1 | 3/2017 | Sanders |
| 2017/0319277 | A1 | 11/2017 | Cantor-Balan et al. |
| 2018/0008355 | A1 | 1/2018 | Mozes et al. |
| 2018/0078332 | A1 | 3/2018 | Mozes et al. |
| 2018/0185103 | A1 | 7/2018 | Mukumoto et al. |
| 2019/0029524 | A1 | 1/2019 | Kopelman et al. |
| 2019/0038367 | A1 * | 2/2019 | Ciriello ................ A61B 34/10 |
| 2019/0076026 | A1 | 3/2019 | Elbaz et al. |
| 2019/0151042 | A1 | 5/2019 | Holman et al. |
| 2020/0163729 | A1 | 5/2020 | Ciriello et al. |
| 2020/0315754 | A1 | 10/2020 | Ciriello et al. |
| 2020/0323540 | A1 * | 10/2020 | Kang .................... A61B 90/37 |
| 2020/0390518 | A1 | 12/2020 | Ciriello et al. |
| 2021/0228317 | A1 * | 7/2021 | Ciriello ................ A61C 1/082 |
| 2022/0142736 | A1 | 5/2022 | Kim |
| 2022/0249187 | A1 * | 8/2022 | Kallenberger ......... A61B 17/00 |
| 2022/0265362 | A1 * | 8/2022 | Marti ....................... G06T 7/85 |
| 2022/0401178 | A1 * | 12/2022 | Polchin ................. A61B 34/20 |
| 2024/0277424 | A1 | 8/2024 | Ciriello et al. |

FOREIGN PATENT DOCUMENTS

| | | |
|---|---|---|
| CN | 107205795 | 9/2017 |
| DE | 10145104 A1 | 1/2003 |
| EP | 2459115 A2 | 6/2012 |
| FR | 2804859 A1 | 8/2001 |
| KR | 102075609 B1 | 2/2020 |
| RU | 2443396 C1 | 2/2012 |
| WO | 2004074324 A2 | 9/2004 |
| WO | 2007072866 A1 | 6/2007 |
| WO | 2011014802 A2 | 2/2011 |
| WO | 2011021192 A1 | 2/2011 |
| WO | 2013172919 A1 | 11/2013 |
| WO | 2014024157 A1 | 2/2014 |
| WO | 2015009856 A2 | 1/2015 |
| WO | 2015026546 | 2/2015 |
| WO | 2015134633 | 9/2015 |
| WO | 2016022347 | 2/2016 |
| WO | 2016040657 | 3/2016 |
| WO | 2016093984 | 6/2016 |
| WO | 2017100828 A1 | 6/2017 |
| WO | 2017130060 | 8/2017 |
| WO | 2018154485 A1 | 8/2018 |
| WO | 2019215511 A2 | 11/2019 |
| WO | 2019215512 A1 | 11/2019 |
| WO | 2021044218 A1 | 3/2021 |
| WO | 2021155045 A1 | 8/2021 |
| WO | 2021257708 | 12/2021 |

OTHER PUBLICATIONS

Fried, et al.: Ablation of Dental Hard Tissues with a Microsecond Pulsed Carbon Dioxide Laser Operating at 9.3-μm with an Integrated Scanner. Proc SPIE Int Soc Opt Eng. 6843: 16 pages (2009).

Fried, et al.: Frailty in older adults: evidence for a phenotype. J Gerontol A Biol Sci Med Sci .; 56(3): M146-56 (2001).

Geomagic Sculpt website http://www.geomagic.com/en/products/sculpt/touch/ (accessed Oct. 2, 2018).

International Searching Authority (European Patent Office), International Search Report re International Application No. PCT/US2024/028050, 3 pages, Aug. 13, 2024.

International Searching Authority (European Patent Office), Written Opinion re International Application No. PCT/US2024/028050, 7 pages, Aug. 13, 2024.

Kauer, et al., Clinical evaluation of effects of low-level lasers on pain during cavity preparation. International Journal of Research - Granthaalayah. 6(10): 81-86 (2018).

Kim, et al., Improved accuracy in periodontal pocket depth measurement using optical coherence tomography. J Periodontal Implant Sci. 47(1): 13-19 (2017).

Le, et al., A non-invasive imaging and measurement using optical coherence tomography angiography for the assessment of gingiva: An in vivo study. J Biophotonics. 11(12) (2018).

Liu, L.; Watanabe, M.; Ichikawa, T., Robotics in Dentistry: A Narrative Review. Dent. J. 2023, 11, 62. https://doi.org/10.3390/dj11030062.

Tsubokawa, et al.: In vitro and clinical evaluation of optical coherence tomography for the detection of subgingival calculus and root cementum. J Oral Sci. 60 (3):418-427 (2018).

United States Patent and Trademark Office, First Action Interview Summary in re U.S. Appl. No. 17/000,175, 6 pages, Jun. 4, 2021.

United States Patent and Trademark Office, Office Action in re U.S. Appl. No. 16/073,057, 16 pages, Jul. 31, 2019.

United States Patent and Trademark Office, Office Action in re U.S. Appl. No. 16/774,679, 13 pages, Jul. 21, 2021.

United States Patent and Trademark Office, Office Action in re U.S. Appl. No. 16/774,679, 13 pages, Oct. 26, 2021.

United States Patent and Trademark Office, Office Action in re U.S. Appl. No. 16/774,679, 16 pages, Oct. 19, 2020.

Visuri, et al.: Shear Strength of Composite Bonded to Er:YAG Laser-prepared Dentin. J Dent Res; 75(1): 599-605 (1996).

Xun Jin, et al., Journal of implantology and applied sciences 2022; 26(1): 27-38 https://doi.org/10.32542/ implantology.2022003.

Yuan, et al.: An automatic tooth preparation technique: A preliminary study; Scientific Reports | 6:25281 | DOI: 10.1038/srep25281, pp. 1-9 (2016).

* cited by examiner

115

117

116

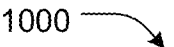

1000

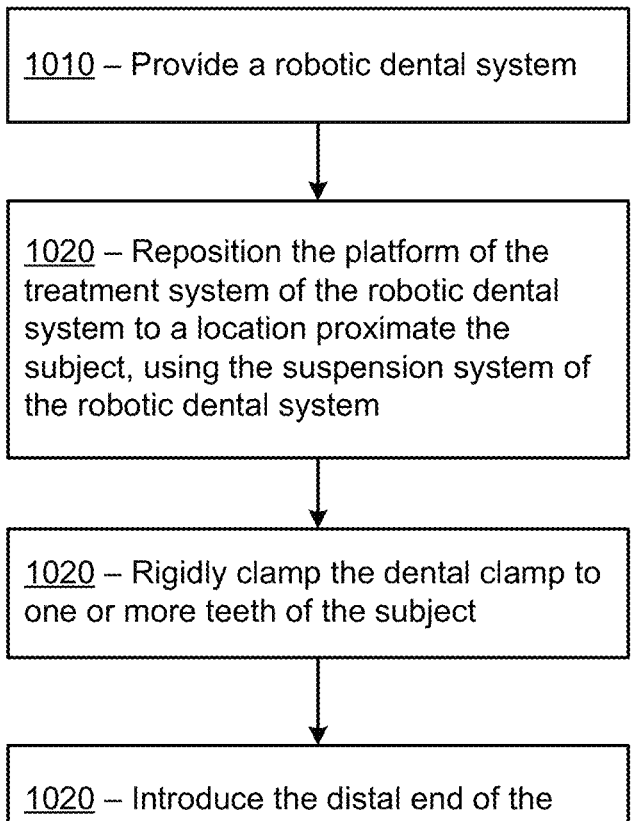

1010 – Provide a robotic dental system

1020 – Reposition the platform of the treatment system of the robotic dental system to a location proximate the subject, using the suspension system of the robotic dental system 1020 – Rigidly clamp the dental clamp to one or more teeth of the subject 1020 – Introduce the distal end of the robotic arm into the mouth of the subject, using the one or more motors of the robotic arm

*FIG. 14*

ROBOTIC DENTAL SYSTEM AND METHOD OF PREPARING FOR A ROBOTIC DENTAL PROCEDURE

CROSS REFERENCE TO RELATED APPLICATIONS

This application is a continuation of U.S. patent application Ser. No. 18/656,502, filed May 6, 2024, titled "Robotic Dental System and Method of Preparing for a Robotic Dental Procedure" and claims a benefit of U.S. Provisional Patent Application No. 63/500,268, filed May 4, 2023, titled "Automated Robotic Dental Treatment System," the entire contents of each of which are hereby incorporated by reference herein, for all purposes.

TECHNICAL FIELD

The present disclosure relates to dental robotics.

RELATED ART

The access to dental care crisis in the United States warrants immediate attention. Over 90% of American adults are affected by dental caries, and approximately 35% of Americans do not visit a dentist annually, with 28% having untreated tooth decay. This widespread dental care avoidance is often attributed to high costs and long appointments. This avoidance contributes to over $45 billion in lost productivity and over 34M lost school hours for young adults and has severe ramifications for individuals' overall health, including increased risks of diabetes, cardiovascular disease, and Alzheimer's disease.

The current state of dentistry has numerous challenges, including a heavy reliance on manual procedures that incur high costs and a limited supply of dental practitioners.

To address these problems we propose the development of a highly precise and accurate robotic tooth preparation system.

The following references may be relevant to the present disclosure: U.S. Pat. Publ. No. 2016/0367343 to Mozes, et al., U.S. Pat. Publ. No. 2016/0354169 to Suttin, and WO 2017/100828 to Zuaiter, et al.

SUMMARY OF EMBODIMENTS

The present disclosure relates to dental robotics, and more particularly to a dental robot that can automatically compensate for weight of a robot arm and can automatically maintain a constant position and orientation of a proximal end of the robot arm, relative to teeth of a human subject, throughout the course of a dental surgery procedure.

In a first aspect, the present disclosure provides a robotic dental system, comprising: a treatment system, a base, and a suspension system.

The treatment system comprises: a robotic arm, a distal end of which is configured to be coupled to an end effector; and a platform, to which a proximal end of the robotic arm is coupled, the platform comprising a coupling portion for rigidly coupling to a dental clamp, which is configured to be rigidly clamped to one or more teeth of a subject, the platform and coupling portion being configured such that, when the dental clamp is rigidly clamped to the one or more teeth and the dental clamp is rigidly coupled to the coupling portion, position and orientation of the platform remain fixed, relative to the one or more teeth.

The suspension system mechanically couples the platform with the base, supports a weight of the treatment system, and is configured such that, when the robotic dental system is operating in a treatment mode, with the dental clamp rigidly clamped to the one or more teeth and the dental clamp rigidly coupled to the coupling portion, the suspension system permits a position and orientation of the platform to change, relative to the base, in response to forces applied by the one or more teeth to the dental clamp, thereby accommodating changes in the position, orientation, and both of the one or more teeth by enabling corresponding changes in the position, orientation, or both of the platform.

In some examples, the robotic dental system is configured to cause the robotic arm to perform a dental procedure on at least one target tooth of the one or more teeth to which the dental clamp is rigidly clamped. The robotic dental system disclosed herein may achieve particularly high accuracy when carrying out a dental procedure on one or more of the teeth clamped by the dental clamp.

In a further aspect, the present invention provides a method of preparing for a robotic dental procedure, the method comprising providing a robotic dental system, which comprises a treatment system, a base, and a suspension system.

The treatment system comprises: a robotic arm, a distal end of which is configured to be coupled to an end effector, the robotic arm comprising one or more motors; and a platform, to which a proximal end of the robotic arm is coupled, the platform comprising a coupling portion, which is rigidly coupled to a dental clamp, which is configured to be rigidly clamped to one or more teeth of a subject, the platform and coupling portion being configured such that, when the dental clamp is rigidly clamped to the one or more teeth and the dental clamp is rigidly coupled to the coupling portion, position and orientation of the platform remain fixed, relative to the one or more teeth.

The suspension system mechanically couples the platform with the base, supports a weight of the treatment system, and is configured such that, when the robotic dental system is operating in a treatment mode, with the dental clamp rigidly clamped to the one or more teeth and the dental clamp rigidly coupled to the coupling portion, the suspension system permits a position and orientation of the platform to change, relative to the base, in response to forces applied by the one or more teeth to the dental clamp, thereby accommodating changes in the position, orientation, and both of the one or more teeth by enabling corresponding changes in the position, orientation, or both of the platform, The method further comprises: rigidly clamping the dental clamp to the one or more teeth of the subject; and, thereafter, introducing the distal end of the robotic arm into a mouth of the subject, using the one or more motors of the robotic arm.

Optionally, the method further includes repositioning the platform of the treatment system to a location proximate the subject, using the suspension system.

Optionally, in any embodiment, the suspension system is passive.

Optionally, in any embodiment, the suspension system is an active suspension system and comprises at least one motor.

Optionally, in any method that includes repositioning the platform, the suspension system is an active suspension system and includes at least one motor, and the repositioning of the platform includes operating the at least one motor of the suspension system, based on input from at least one force sensor, to move the platform to the location proximate the subject.

Optionally, in any embodiment with an active suspension system, when the robotic dental system is operating in a treatment mode, the at least one motor is operated based on input from at least one force sensor so as to cause the position, orientation or both of the platform to change, relative to the base, in response to the forces applied to the dental clamp, thereby permitting corresponding changes in the position, orientation, or both of the one or more teeth.

Optionally, in any embodiment with an active suspension system, when the robotic dental system is operating in a compliant mode, the at least one motor is operated, based on input from at least one force sensor, so as to cause the position, orientation or both of the platform to change, relative to the base, in response to forces applied to the treatment system by an operator of the robotic dental system, thereby permitting the operator to reposition the treatment system in a desired arrangement.

Optionally, any embodiment further includes the clamp, rigidly coupled to the coupling portion.

Optionally, in any embodiment that includes the clamp, the dental clamp is configured to be rigidly clamped to a plurality of teeth of the subject, and the robotic arm is operable to address at least two of the plurality of teeth.

Optionally, in any embodiment, the robotic arm is configured so as to be insertable into a mouth of the subject separately from the dental clamp.

Optionally, in any embodiment, the robotic dental system is configured to cause the robotic arm to perform a dental procedure on at least one target tooth of the one or more teeth to which the dental clamp is rigidly clamped.

Optionally, in any embodiment, the robotic arm has at least six degrees of freedom.

Optionally, in any embodiment, the robotic arm has more than six degrees of freedom.

Optionally, in any embodiment, the robotic arm comprises a plurality of robotic joints.

Optionally, in any embodiment, the robotic arm comprises at least four robotic joints.

BRIEF DESCRIPTION OF THE DRAWINGS

The present disclosure will be more fully understood by referring to the following Detailed Description of Specific Embodiments in conjunction with the Drawings, in which:

FIG. 14 is a flow chart illustrating a method of preparing for a robotic dental procedure according to a further aspect of this disclosure.

DETAILED DESCRIPTION OF SPECIFIC EMBODIMENTS

An automated robotic dental treatment system described herein may be capable of achieving an accuracy of at least about 50 microns ($\mu$m) in automating tooth preparation for dental crowns and other dental procedures. This accuracy is an order of magnitude more accurate than current dental robotic systems, surpassing the performance of existing surgical robots, such as Yomi (NeoCis, Inc., Miami, FL, USA) and THETA (Hangzhou Jianjia Robot Co., Ltd., Hangzhou, China), which only have an accuracy of about 750-1100 $\mu$m.

In order to achieve high accuracy, two conventional approaches have been to, one, dynamically register a robot or, two, make the robot so small and light weight that it can completely fit onto a target tooth.

A robot is an automated machine capable of executing a specific task with minimal human intervention (i.e., autonomously) while maintaining speed and precision. A serial manipulator is a type of robot that includes a series of links connected by motor-actuated joints that extend from a base to an end effector. The motor-actuated joints may include but are not limited to linear joints, rotational joints, and spherical joints, and such joints may be provided with sensors for one or more of position, orientation, or force, such as linear transducers, haptic sensors, torque sensors, accelerometers, gyroscopes, and magnetic or visual indicators for external sensors.

Figure 1:
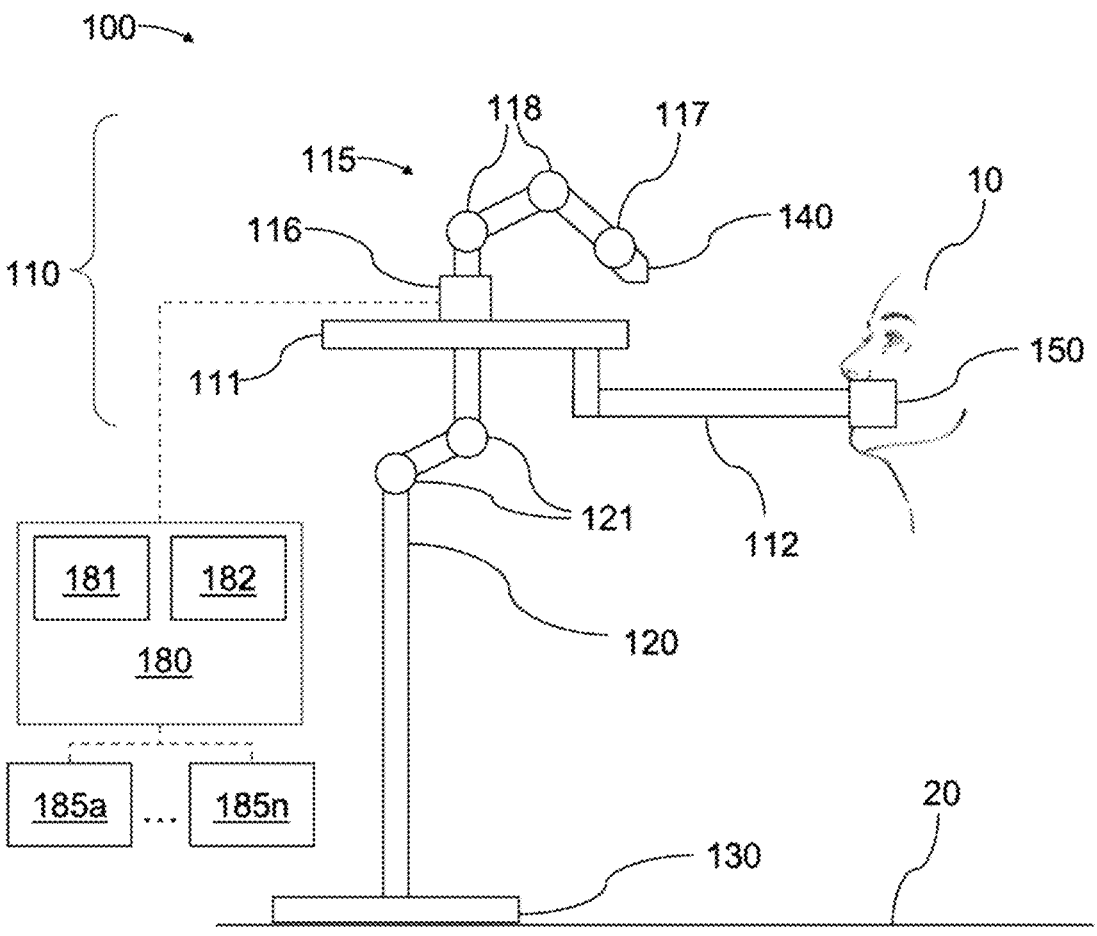
FIG. 1 is a schematic side view of an example of a robotic dental system according to a first aspect of this disclosure.
Figure 3:
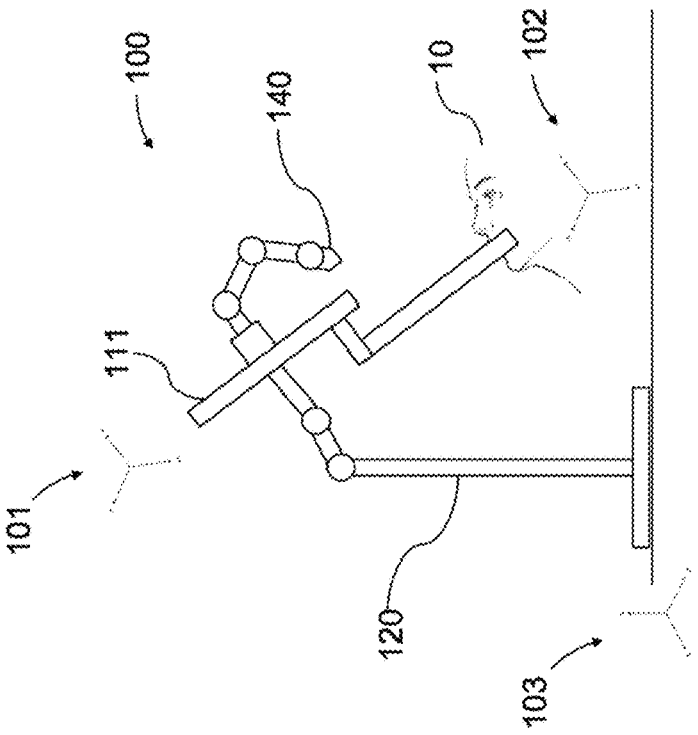
FIGS. 2 and 3 illustrate the robotic dental system of FIG. 1 with a subject in two different positions and orientations.
Figure 2:
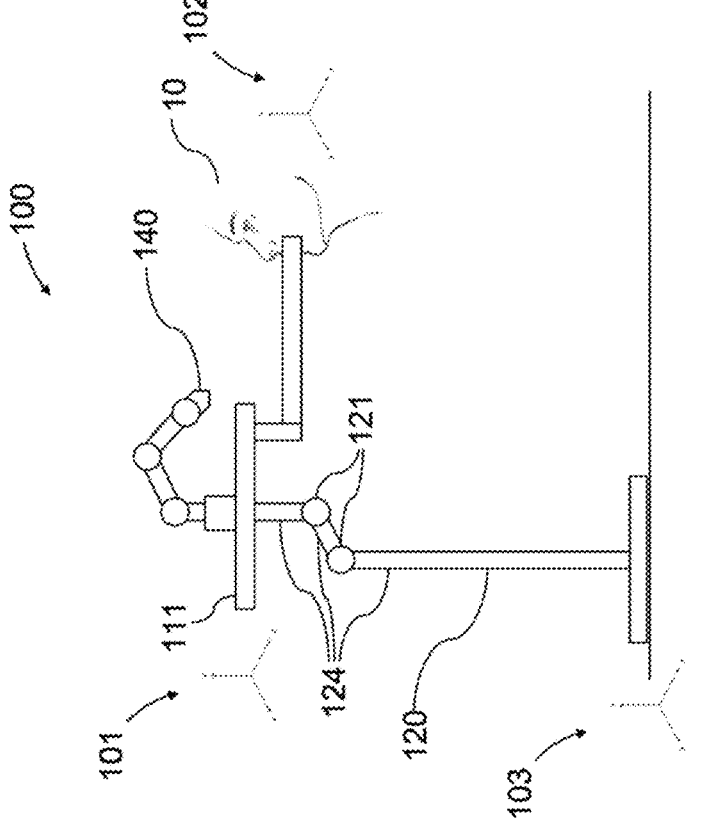

Reference is now direction to FIGS. 1-3, which are schematic side views of an example of a robotic dental system 100 according to a first aspect of this disclosure. FIGS. 1-3 show a subject 10 (e.g. a patient) in different positions and orientations, during treatment with the robotic dental system 100.

As may be seen from FIG. 1, the robotic dental system 100 comprises a robotic arm 115, and a platform 111, to which a proximal end 116 of the robotic arm 115 (which may, in some examples, be referred to as the root, shoulder, or base of the robotic arm 115) is attached. A distal end 117 of the robotic arm 115 is coupled to an end effector 140, which is used for carrying out a dental procedure on subject 10. Accordingly, the robotic arm 115 may, in examples, be referred to as a "treatment arm" and the end effector 140 can, for example, be a dental drill. The distal end 117 of the robotic arm 115 can comprise a suitable receptacle for coupling to the end effector 140. The receptacle can, for example, comprise a mechanical interface to ensure the end effector is coupled to the distal end 117 with the right orientation. Examples of end effectors suitable for use with the robotic treatment systems of this disclosure are described in U.S. patent application Ser. No. 17/054,442, filed Jun. 22, 2021, Ser. No. 17/054,445 filed Nov. 10, 2020, and Ser. No. 18/066,892, filed Dec. 15, 2022.

As indicated in FIG. 1, the platform 111 and the robotic arm 115 are part of a treatment system 110 of the robotic dental system 100. As will be explained in more detail below, the treatment system 110 is able (with the aid of a suspension system 120 of the robotic dental system 100) to accommodate movement by the subject 10 during treatment, thereby promoting the comfort of the subject 10 during treatment, while maintaining the accuracy of the robotic arm 115.

As shown in FIG. 1, the platform 111 comprises a coupling portion 112, which is rigidly (and removably/releasably) coupled to a dental clamp 150. By "rigidly coupled", it is meant that such coupling maintains the coupling portion 112 in a fixed position and orientation relative to the dental clamp 150, even if the subject 10, and therefore the dental clamp 150, changes position or orientation. As a result of the rigid coupling, the platform 111 likewise remains in a fixed position and orientation relative to the dental clamp 150. Although in the example shown in FIGS. 1-3 the coupling portion 112 is shown as being in the form of an arm extending from the platform 111, this is by no means essential and the coupling portion 112 can have any suitable structure to allow rigid coupling to a particular design of dental clamp 150. For example, the coupling portion 112 and the dental clamp 150 can comprise any suitable coupling features that permit one to rigidly couple with the other such as a pin, a threaded feature, a clip, a magnet, a nut, a bolt, a catch, a clasp, or any combination thereof.

The platform 111 functions to maintain various fixtures that are attached thereto in a fixed position and orientation relative to each other. Accordingly, the platform 111 can, for example, be a substantially rigid structure. While in the example of a robotic dental system 100 shown in FIG. 1, the fixtures attached to the platform 111 include the dental clamp 150 (by way of the coupling portion 112 of the platform 111) and the robotic arm 115, it will be appreciated that, in other examples, the platform 111 may be configured so that additional fixtures may be rigidly coupled thereto, such as further robotic arms, or mechanical arms that can be coupled to intraoral scanning devices (e.g., as described in WO2022/212507A1). Furthermore, while in the example of a robotic dental system 100 shown in FIG. 1, the platform 111 is configured with a generally planar main body, this is by no means essential and in other examples the platform 111 may have any suitable shape that permits it to maintain fixtures coupled thereto in a fixed position and orientation.

Though not shown in detail in FIG. 1, dental clamp 150 is in turn rigidly (and removably) coupled to one or more teeth of the subject 10. Examples of suitable clamps for use with the robotic dental system 100 are described in U.S. patent application Ser. No. 17/054,442, filed Jun. 22, 2021, Ser. No. 17/054,445 filed Nov. 10, 2020, and Ser. No. 18/066,892, filed Dec. 15, 2022. When clamping to the one or more teeth of the subject 10, the dental clamp 150 directly contacts and clamps onto the teeth themselves. As a result, the position and orientation of the platform 111 remain fixed, relative to the one or more teeth clamped by the dental clamp 150 (even if the subject 10, and therefore the dental clamp 150, changes position or orientation). Such an arrangement may assist the robotic arm 115 in accurately addressing the teeth of subject 10, particularly (but not exclusively) where the robotic dental system 100 is configured (e.g., by suitable programming of the processor(s) 181 of control system 180) to perform a procedure on one or more of the teeth that are clamped by the dental clamp 150.

As be seen from FIG. 1, the robotic dental system 100 further comprises a base 130, and a suspension system 120, which mechanically couples the platform 111 with the base

Figure 8:
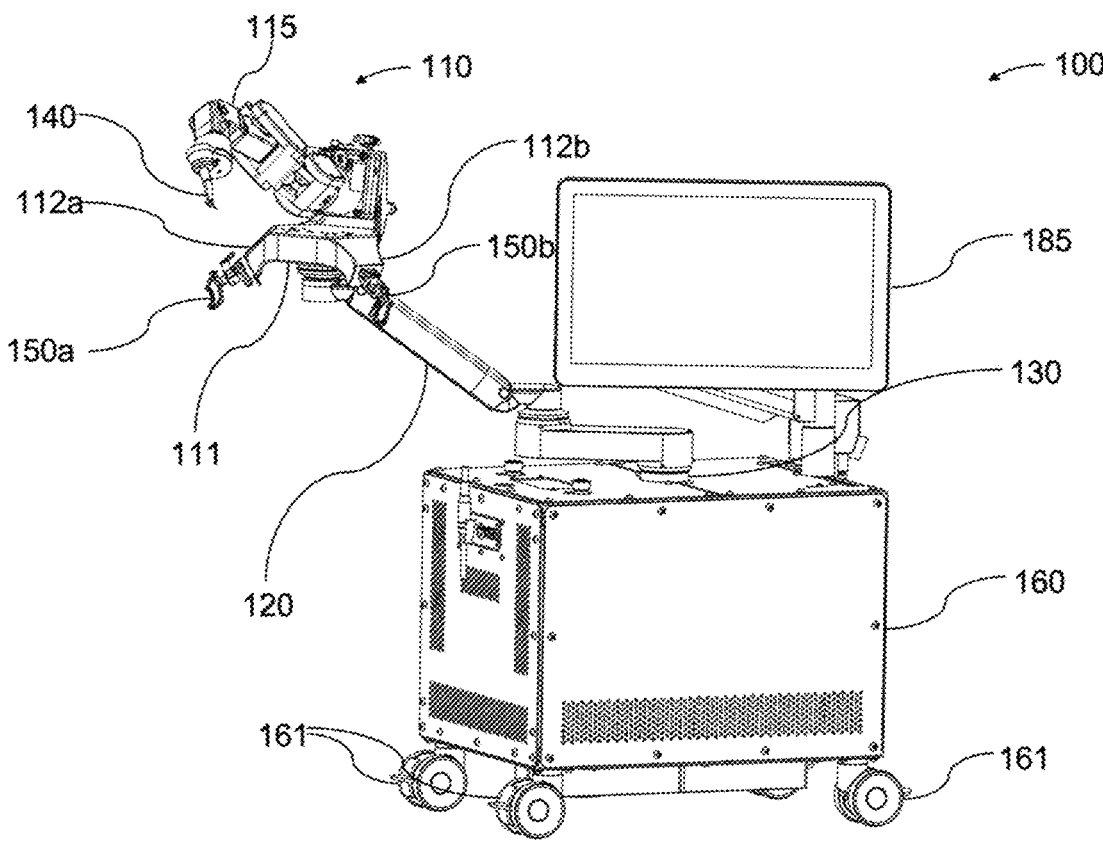
FIG. 8 is a perspective view of a further example of a robotic dental system according to the first aspect of this disclosure.
Figure 9:
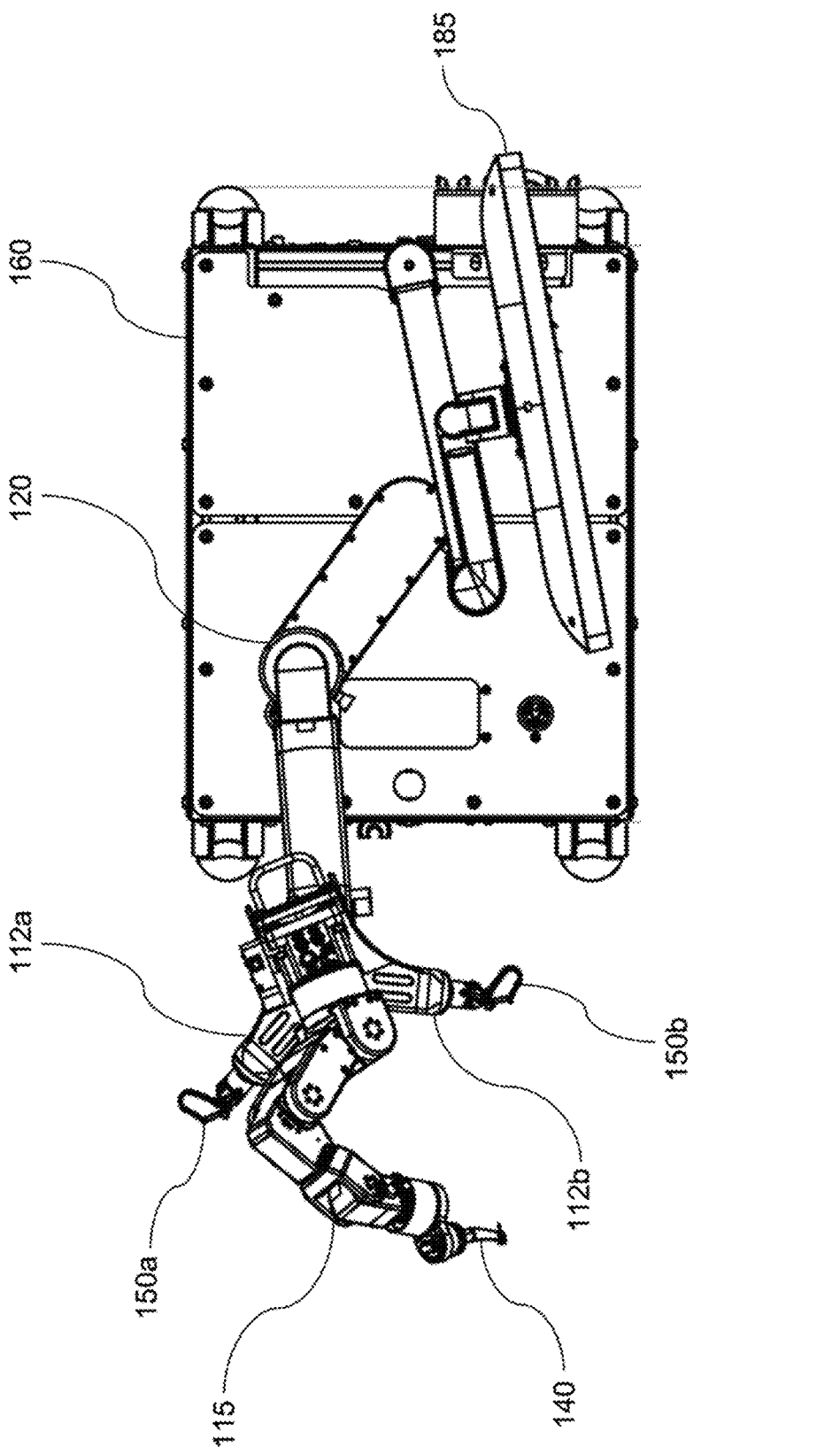
FIG. 9 is a top view of the robotic dental system of FIG. 8.
Figure 10:
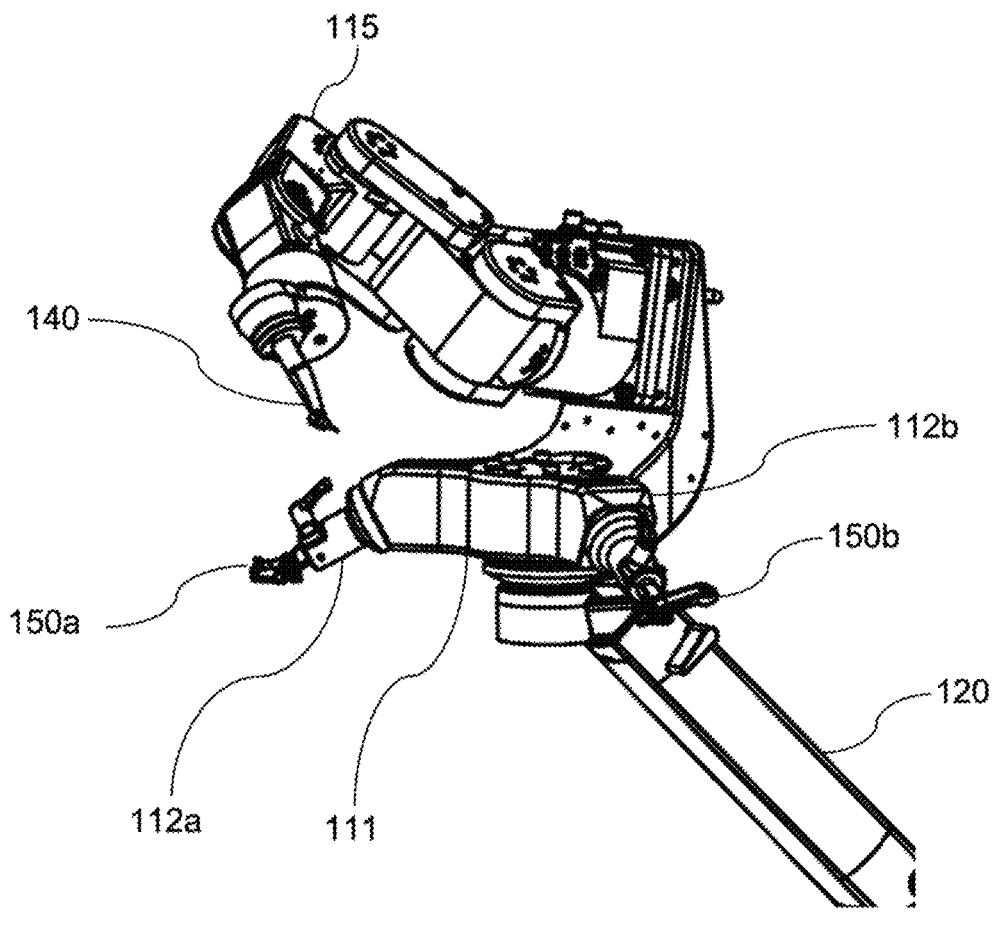
FIG. 10 is a perspective view of the treatment system of the robotic dental system shown in FIGS. 8 and 9.
Figure 11:
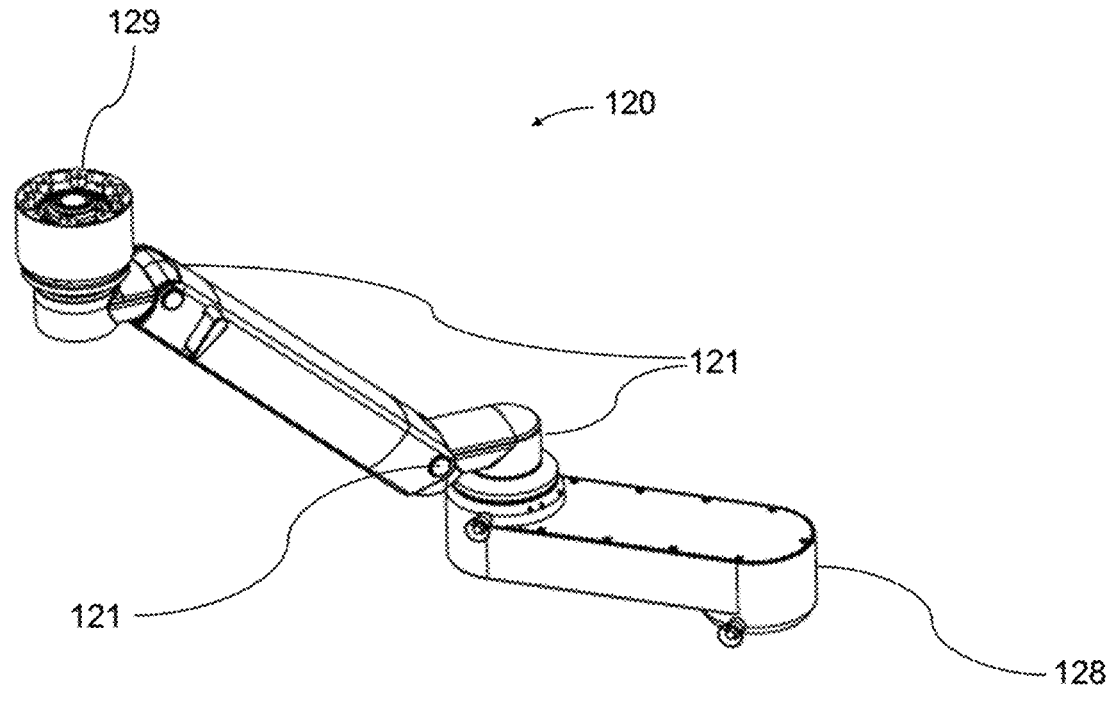
FIG. 11 is a perspective view of the suspension system of the robotic dental system shown in FIGS. 8 and 9.
Figure 12:
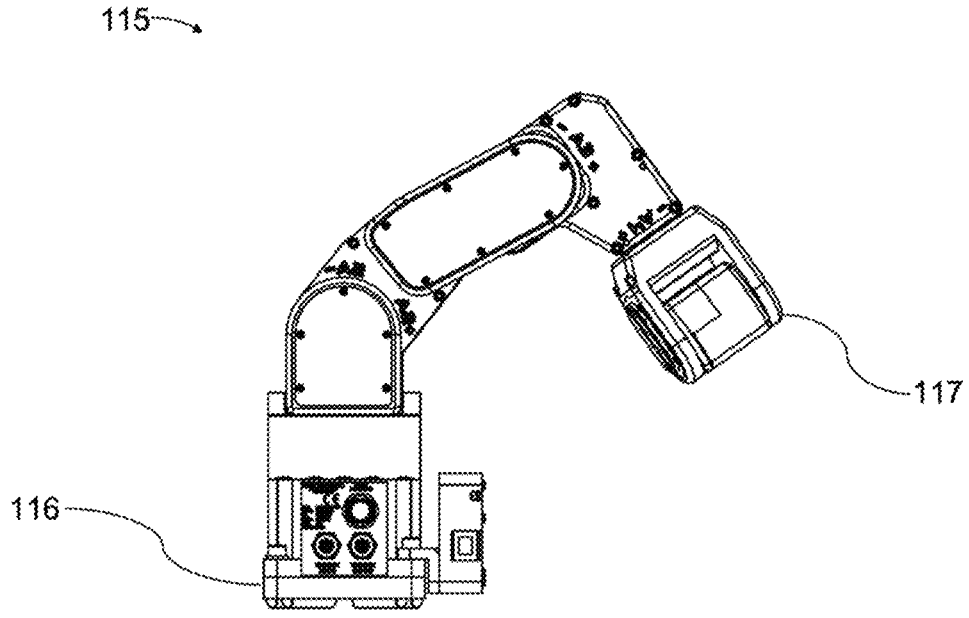
FIG. 12 is a side view of the robotic arm of the robotic dental system shown in FIGS. 8 and 9.

130. The base 130 of the robotic dental system 100 remains generally stationary during a procedure and hence remains in a generally fixed position and orientation with respect to the environment in which the robotic dental system 100 is operating (e.g., a room or space in a dental practice where the procedure is being carried out). In the example shown in FIG. 1, the base 130 is fixed to the floor 20 (or to the ground). However, this is by no means essential and in other examples, the base 130 may simply rest on the floor 20 (or the ground), for instance on wheels (e.g., having casters) provided on the base 130. In still other examples, such as that shown in FIGS. 8-9, the base 130 may be fixed to a moveable module that supports the treatment system 110 and the suspension system 120 and, optionally, provides other components of the robotic dental system 100), As further shown in FIG. 1, the robotic dental system 100 may additionally comprise a control system 180 that comprises at least one processor 181. The control system 180 governs the operation of various subsystems within the robotic dental system 100 (e.g., as a result of suitable programming of the at least one processor 181). In particular, as shown by the dashed line in FIG. 1, the control system 180 may be in data communication with the robotic arm 115 so as to control the movement thereof. As shown in FIG. 1, the control system 180 additionally comprises computer-readable storage medium 182, which stores instructions for execution by the at least one processor 181 so that the robotic dental system 100 operates as described herein.

In some examples, the control system 180 may be integrated into (and therefore form a part of) the robotic dental system 100. However, in other examples, the robotic dental system 100 may be configured such that it can be provided to an end-user without an integrated control system 180. In such cases the end user might, for example, use their own general purpose computer (such as a laptop) as a control system 180 for the robotic dental system 100, for instance after downloading and installing suitable software on the general purpose computer.

Returning to FIG. 1, it may be noted that the control system 180 is additionally in data communication with one or more user input devices 185a-185n that, for example, enable an operator of the robotic dental system 100 to provide instructions to the control system 180 that are followed by the robotic dental system 100, for instance by the robotic arm 115 (or other subsystems of the robotic dental system 100). As will be appreciated, various kinds of user input devices 185a-185n can be utilized, such as keyboards, joysticks, pointing devices (e.g., a computer mouse or trackball), touchscreen displays etc.

Reference is now directed to FIGS. 2 and 3, which are schematic side views of the robotic dental system 100 of FIG. 1 that show a subject 10 (e.g. a patient) in respective different positions and orientations, and thereby enable the function of the suspension system 120 to be more fully understood.

FIG. 2 shows the subject 10 in a first position and orientation within a room or other environment where a dental procedure is being performed by robotic dental system 100. Accordingly, FIGS. 2 and 3 both show the robotic dental system 100 while it is operating in a "treatment mode". During such a treatment mode the robotic dental system 100 may, for example, operate substantially autonomously (e.g., receiving, at most, limited and/or high-level input from the operator). In particular, the robotic arm 115 may operate substantially autonomously to carry out a dental procedure on one or more target teeth within the mouth of the subject 10 (which, as noted above, may be one or more of the teeth clamped by the dental clamp 150). Such a treatment mode can be distinguished from, for example, a setup mode (e.g., where the robotic dental system 100 is being moved into position). As shown in both FIGS. 2 and 3, the dental clamp 150 is clamped onto one or more teeth of the subject 10 and therefore the position and orientation of the platform 111 remain fixed, relative to the one or more teeth clamped by the dental clamp 150.

FIG. 3 shows the subject 10 a short time later, when he/she is in a second, different position and orientation within the environment. As may be appreciated from a comparison of FIGS. 2 and 3, this change in position and orientation of the subject 10 is accommodated by a corresponding change in the position and orientation of the platform 111. As is also apparent from a comparison of FIGS. 2 and 3, the platform 111 is able to change its position and orientation as a result of the action of the suspension system 120, specifically, by articulations of joints 121 in the suspension system 120.

FIGS. 2 and 3 additionally show a frame of reference 101 for the platform 111 and a frame of reference 102 for the subject 10. As is apparent from FIGS. 2 and 3, the spatial relationship between these frames of reference 101, 102 is maintained when the subject 10 moves. Because the robotic arm 115 is rigidly coupled to the platform 111, whose frame of reference 101 is in a fixed spatial relationship with the frame of reference 102 for the subject 10, the robotic arm 115 can maintain its registration relative to the teeth of the subject 10, even when the subject 10 moves during a procedure.

While in the particular example shown in FIGS. 1-3, the suspension system 120 comprises a series of linkages connected by joints 121, it will be appreciated that this particular structure is by no means essential and in other examples the suspension system may have any suitable structure that permits the position and orientation of the platform 111 to change, relative to the base 130, in response to forces applied by clamped tooth or teeth to the dental clamp 150, thereby accommodating changes in the position and orientation of the clamped tooth or teeth by enabling corresponding changes in the position and orientation of the platform 111. For example, suitable structures might comprise spring-loaded linkages, gimbals, linkages connected by friction joints and the like. Moreover, the suspension system 120 is not limited to a linear structure. Accordingly, in other examples, the suspension system could, for instance, include linkages in more complex arrangements, such as, for example, a four-bar linkage arrangement.

It should be appreciated that the suspension system 104 supports the weight of the treatment system 110, including the platform 111 and the robotic arm 115, so that they feel nearly weightless to the subject 10. Consequently, the platform 111 can "float" with respect to the floor 20 (or the ground). Hence (or otherwise), a relatively large and/or complex robotic arm 115 may be utilized in the robotic dental system 100. For instance, the robotic arm 115 may have sufficient reach to be able to operate on several different teeth within the mouth of the subject 10, without needing the system to be reconfigured. In addition, or instead, the robotic arm 115 may, for example, be configured to permit movement of the distal end 117 in six degrees-of-freedom (DOF) with rotation (e.g., roll, pitch, yaw) and 3D translation of the end effector 140 with respect to the proximal end 116 of the robotic arm 115. Moreover, in some examples the robotic arm 115 may have more than six degrees-of-freedom, providing it with redundant degrees of freedom that can be used to provide improved access to the subject's mouth and/or the tooth/teeth to be treated (e.g., by enabling the robotic arm 115 to adopt an arrangement that is wider in the horizontal plane than the vertical plane, so as to better fit between the upper and lower dental arches), and/or to assist the operator in using the robotic dental system 100 (e.g., by enabling the robotic arm 115 to adopt an arrangement that improves the operator's visibility of the tooth or teeth being treated by the robotic dental system 100).

It should also be appreciated that the weights of the suspension system 120, the treatment system 110 (including the robotic arm 115 and the platform 111) may, in some examples, be selected so that the center of gravity of the full assembly of such components is above the base 130, for instance, even when the distal end 117 of the robotic arm 115 and/or the dental clamp 150 are fully extended away from the platform 111.

It should further be appreciated that the suspension system 120 may also (or instead) have redundant degrees of freedom (for instance, more than 6 degrees of freedom), for example allowing for its elbow to be moved into configurations that are convenient for an operator or subject.

Still further, it should be noted that the suspension system 120 may be configured either as a passive system or an active system. In a passive system, the accommodating movements of the suspension system 120 are not caused by powered components, but rather the suspension system 120 permits external forces that are applied to the treatment system 110 to mechanically cause the position and orientation of the platform 111 to change. For example, when subject 10 applies a force to the dental clamp 150 by attempting to move, that force is mechanically transmitted through the coupling portion 112, to the platform 111 and then to the suspension system 120, which moves, thus permitting the platform 111 to move, thereby enabling the subject 10 to move. In addition, where the suspension system 120 is configured as a passive system, an operator may be able to manually reposition the treatment system 110 during setup, for example by pushing and/or pulling the treatment system 110 so that it moves into a desired position and orientation relative to the subject 10.

Where, by contrast, the suspension system 120 is an active system, the accommodating movements of the suspension system 120 are caused by one or motors that form part of the suspension system 120. Such motors may, for example, comprise linear motors that cause linkages to translate relative to one another, and/or may comprise rotational motors that cause linkages to rotate relative to one another. In some examples, the suspension system 120 may essentially be a robotic arm or manipulator, whose movement is based on the output of force sensors.

Figure 4:
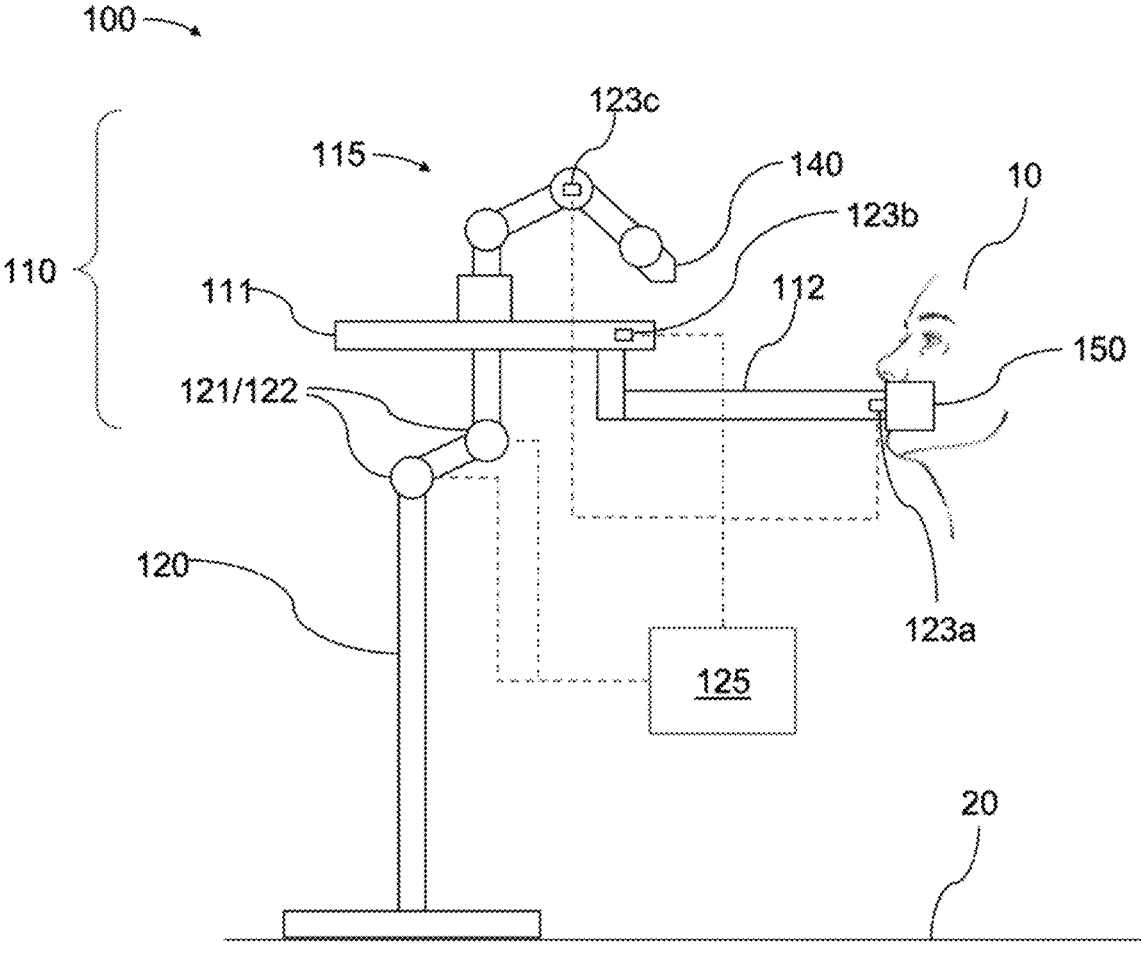
FIG. 4 is schematic side view of the robotic dental system of FIG. 1, when implemented with an active suspension system.

An example of a robotic dental system 100 with an active suspension system 120 is shown in FIG. 4. As is apparent, the robotic dental system 100 of FIG. 4 is a modified version of the robotic dental system 100 of FIGS. 1-3. As is apparent, the robotic dental system 100 of FIG. 4 differs from that of FIGS. 1-3 in that it comprises several force sensors 123*a*-123*c*. As indicated by dashed lines in FIG. 4, the respective outputs from these force sensors 123*a*-123*c* are communicated to a controller 125 (e.g., comprising a processor and/or logic circuitry) for the suspension system 120. The controller 125 operates motors 122 that form part of the suspension system 120 so as to cause the position and/or orientation of the platform 111 to change, relative to the base 130, in response to forces sensed by the force sensors 123*a*-123*c*. In some examples, the controller 125 may operate the motors 122 to cause movements of the suspension system 120 that are expected to reduce (or minimize) the forces sensed by the force sensors 123a-123c. In such examples, the suspension system 120 may compliantly move in response to forces sensed by the force sensors 123a-123c.

It may be noted that, in the particular example shown in FIG. 4, the motors 122 are rotational motors that are integrated into the joints 121 of the suspension system 120; however, this is of course not essential and the motors 122 could be of any suitable type or have any suitable arrangement that can cause the position and/or orientation of the platform 111 to change, relative to the base 130, in response to forces sensed by the force sensors 123a-123c.

It may also be noted that force sensor 123a is integrated into coupling portion 112. It can therefore sense forces applied to the dental clamp 150 by the subject 10 during treatment. Accordingly, the output from force sensor 123a can be used, when the robotic dental system 100 is operated in a treatment mode, to control suspension system 120 to accommodate movement by the subject 10.

It may also be noted that force sensors 123b and 123c are integrated into, respectively, platform 111 and robotic arm 115. The output from one or both of such sensors can, for example, indicate that an operator is applying force to the treatment system 110. Hence, or otherwise, their output can be used when the robotic dental system 100 is operating in a compliant mode (which can, for instance, be a setup mode). More particularly, the output from one or both of force sensors 123b and 123c can be used to operate the motors 122 of the suspension system 120 to cause the position and/or orientation of the platform 111 to change, so that an operator is able to reposition the treatment system 110 in a desired location. It should be noted that, although three force sensors 123a-123c and corresponding motors are shown and described, other embodiments can include other numbers of force sensors and/or corresponding motors.

Figure 6:
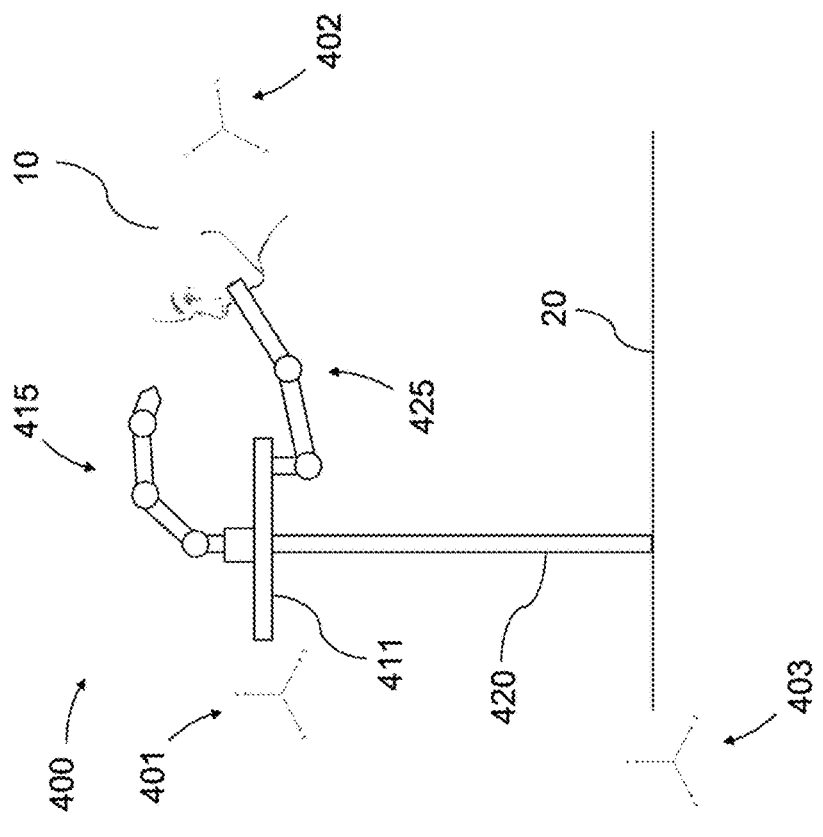
FIGS. 5 and 6 are schematic side views of a comparative example of a robotic treatment system, with a subject in different positions and orientations.
Figure 5:
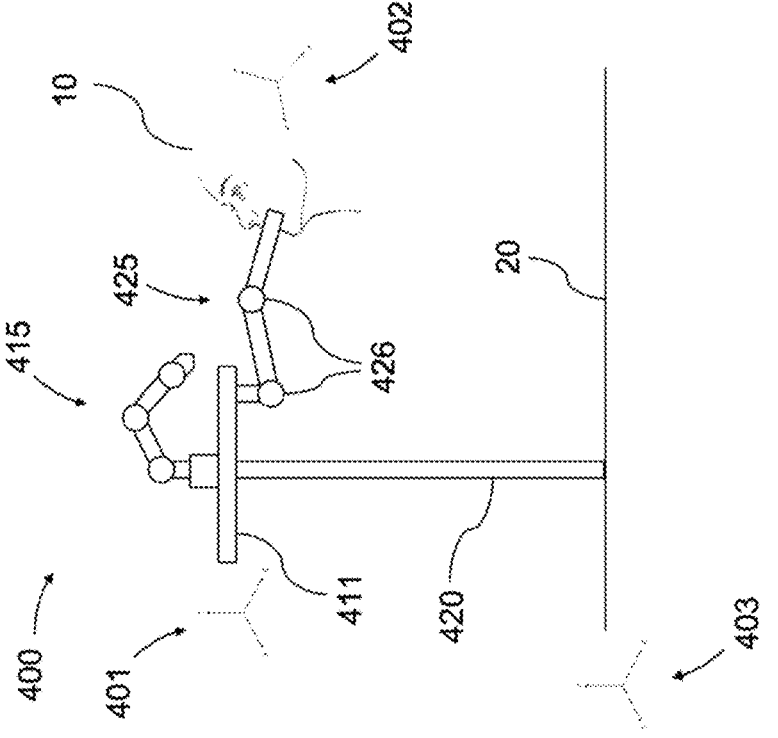

The advantages of the robotic dental systems of FIGS. 1-4 can be more fully appreciated by contrast with the comparative example of a robotic dental system illustrated in FIGS. 5 and 6. As shown, the system 400 of the comparative example includes a platform 411, which is supported above the floor 20 by a rigid support 420, and a robotic treatment arm 415, which is rigidly coupled to the platform 411 and which carries out a procedure on the subject 10. Notably, the system 400 of FIGS. 5 and 6 additionally includes a measurement arm 425, which is coupled to the subject 10, for example to the subject's teeth and/or jaw. The measurement arm 425 articulates freely (with the aid of articulated joints 426) when the subject 10 moves, and sensors within the measurement arm (not shown) determine the current position of the measurement arm. A controller translates the information from the sensors of the measurement arm 402 into compensatory movement of the treatment arm 415 to account for movements of the subject 10.

FIGS. 5 and 6 illustrate the frame of reference 401 of the platform 411 and the frame of reference 402 of the subject 10 at respective, different positions and orientations of the subject 10. Notice that the subject's frame of reference 402 is different between FIGS. 5 and 6, owing to the movement of the subject 10. However, the frame of reference 401 of the platform 411 is the same in both FIGS. 5 and 6. That is, the frame of reference 401 of the platform 411 does not change, in response to movement of the subject 10. Instead, the relationship of the frame of reference 401 of the platform 411 remains constant, relative to the frame of reference 403 of the floor/ground 20.

The system 400 of FIGS. 5 and 6 may generally be characterized as tracking movement of the subject 10 and actively compensating for such movement of the subject by controlling the movement of the robotic treatment arm 415 based on the measured movement of the subject 10. Such active compensation can introduce two errors into the subject tracking system. First, a measurement error occurs in the measurement arm 425. Second, a feedback delay occurs when processing the data and articulating the treatment arm 415, resulting in lag and additional errors as the subject moves.

Robotic systems according to the present disclosure, such as the robotic treatment systems 100 described above with reference to FIGS. 1-4, can avoid the problems inherent in any system incorporating active feedback and correction and can avoid measurement errors and feedback delays by using a passive subject tracking system that does not require any active elements to react to and compensate for subject movement. In the robotic treatment systems 100 described above with reference to FIGS. 1-4 and other embodiments of the present disclosure, the subject can be rigidly attached to the system, preserving the spatial relationship relative to the base of the treatment arm, and the movable suspension system can carry the weight of the treatment such, including the platform 111 and all that is attached to thereto, such as the robotic arm 115, end effector 140, coupling portion 112, and dental clamp 150.

Figure 7:
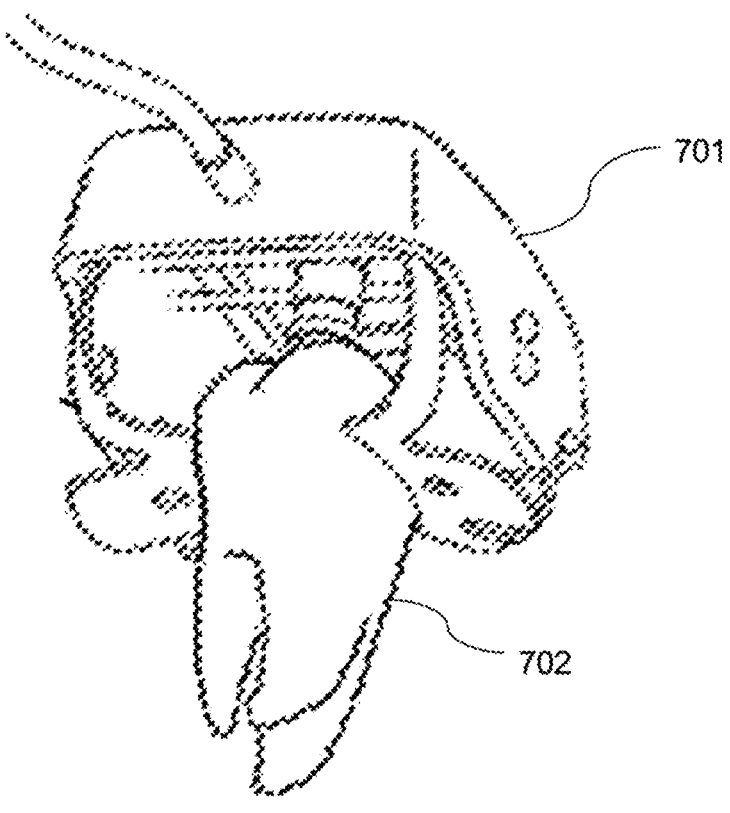
FIG. 7 is a perspective view of a miniature robotic dental treatment system, according to a comparative example.

The robotic treatment systems 100 of FIGS. 1-4 and other embodiments of the present disclosure also differentiate from robotic dental systems that are so small that they sit on the subject's tooth 702, such as the system 701 shown in FIG. 7. Such a system (to the extent it could practically be implemented) would have no need of a suspension system, such as the suspension system 120 shown in FIGS. 1-3. Indeed, including a suspension system in such a robotic dental system would be antithetical to the fundamental design principle of the robotic dental system, which is to make the robotic dental system so lightweight that no support from, or engagement with, the ground is necessary. The examples of a robotic dental system 100 of FIGS. 1-4 and other embodiments of the present disclosure take a significantly different approach to such robotic dental systems that sit on a subject's tooth. Because the examples of a robotic dental system 100 of FIGS. 1-4 include a suspension system 120 that makes the treatment system 110 nearly weightless to the subject 10, it is possible for the treatment system 110 to include a sizable robotic arm 115, whose base is rigidly coupled to a platform 111 located outside the subject's mouth. Such an arrangement may afford the robotic arm 115 a large range of motion and/or the ability to treat multiple teeth without needing to be repositioned. In addition (or instead), such an arrangement can include larger (and therefore more powerful) motors and affords more flexibility over the types of end effector 140 that can be utilized by the robotic arm 115.

Figure 13A:
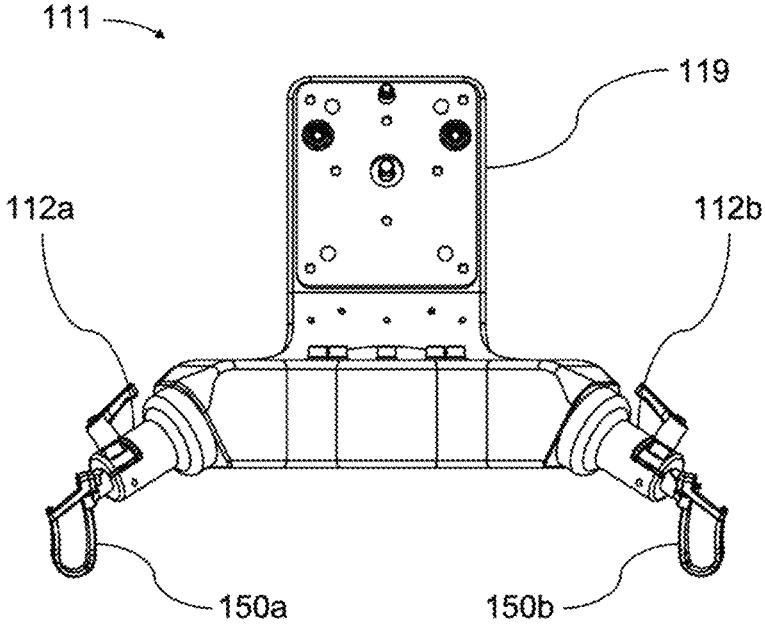
FIGS. 13A and 13B are, respectively, front and perspective views of the platform of the robotic dental system shown in FIGS. 8 and 9.
Figure 13B:
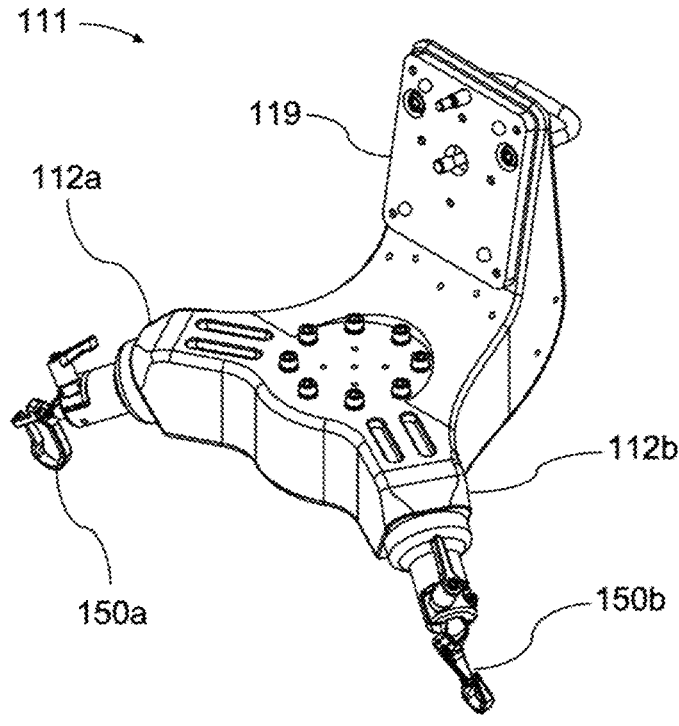

Attention is now directed to FIGS. 8-13B, which show a further, more detailed example of a robotic dental system 100 in accordance with the first aspect of this disclosure. Like the robotic dental system 100 shown in FIGS. 1-3, the robotic dental system 100 of FIGS. 8-13 comprises a treatment system 110 that includes a robotic arm 115, whose distal end 117 is configured to be coupled to an end effector 140, and whose proximal end 116 is coupled to a platform 111 of the treatment system 110. The robotic arm 115 of the robotic dental system 100 of FIGS. 8-13 is shown in further detail in FIG. 12, which is a side view of the robotic arm 115 in isolation, whereas the platform 111 of the robotic dental system 100 of FIGS. 8-13 is shown in further detail in FIGS. 13A and 13B, which are, respectively front and perspective views of the platform 111 in isolation (though with dental clamps 150a, 150b attached). FIGS. 13A and 13B in particular show the mechanical interface 119 that enables the proximal end 116 of the robotic arm 115 to rigidly couple to the platform 111.

In addition, like the robotic dental system 100 of FIGS. 1-3, the treatment system 110 of the robotic dental system 100 of FIGS. 8-13 is supported by a suspension system 120 that couples the platform 111 of the treatment system 110 to a base 130. The suspension system 120 of the robotic dental system 100 of FIGS. 8-13 is shown in further detail in FIG. 11, which is a perspective view of the suspension system 120 in isolation. The suspension system 120 of the robotic dental system 100 of FIGS. 8-13 enables the treatment system 110 to accommodate movement by the subject 10 in the essentially the same manner described above with reference to FIGS. 2-3, and accordingly includes a number of joints 121 that articulate to permit movement of the platform 111, thereby accommodating movement by the subject 10. However, in contrast to the robotic dental system 100 of FIGS. 1-3, the platform 111 of the robotic dental system 100 of FIGS. 8-13 includes two coupling portions 112a, 112b that can be rigidly (and releasably) coupled to respective dental clamps 150a, 150b, as seen most clearly in FIGS. 13A and 13B. In the example shown, the two dental clamps 150a, 150b accommodate the opposing sides (left and right) of a patient; however, in other examples multiple (i.e., two or more) dental clamps may accommodate operation of the robotic dental system 100 by the operator.

In further contrast to the robotic dental system 100 of FIGS. 1-3, the base 130 of the robotic dental system 100 of FIG. 8-13 is not fixed to the ground, but rather is coupled to a mobile cart 160 having a number of wheels 161 that permit an operator to move the robotic dental system 100 to a desired location.

In the particular example shown in FIGS. 8-13, a user interface module 185 (best seen in FIG. 8) for the robotic dental system 100 is mounted on the mobile cart 160. The user interface module 185 can present various kinds of information to the operator of the robotic dental system 100, such as information regarding the status of the robotic dental system 100, information regarding the procedure to be carried out on the subject 10, and/or information regarding the dental anatomy of the subject 10. As shown in FIGS. 8-13, the user interface module 185 can, for example, comprise a computer monitor.

The mobile cart 160 may, in some examples, include various elements such as: a rechargeable power supply in electrical communication with an electric panel that provides charging ports for portable electronic devices; converters, transformers and surge protectors for a plurality of AC and DC receptacles that provide a power source for the equipment on-board the mobile cart 160, such as the user interface module 185 and/or one or more computers storing application specific software for the user interface module 185.

Reference is now directed to FIG. 14, which is a flow diagram that illustrates a method 1000 of preparing for a robotic dental procedure according to a further aspect of this disclosure.

As shown in FIG. 14, the method 1000 comprises a step 1010 of providing a robotic dental system (such as one of the examples of a robotic dental system 100 described herein) that comprises: a treatment system, which comprises: a robotic arm, a distal end of which is configured to be coupled to an end effector, the robotic arm comprising one or more motors; and a platform, to which a proximal end of the robotic arm is coupled, the platform comprising a coupling portion, which is rigidly coupled to a dental clamp, which is configured to be rigidly clamped to one or more teeth of a subject, the platform and coupling portion being configured such that, when the dental clamp is rigidly clamped to the one or more teeth and the dental clamp is rigidly coupled to the coupling portion, the position and orientation of the platform remain fixed, relative to the one or more teeth; a base; and a suspension system, which mechanically couples the platform with the base, supports the weight of the treatment system, and is configured such that, when the robotic dental system is operating in a treatment mode, with the dental clamp rigidly clamped to the one or more teeth and the dental clamp rigidly coupled to the coupling portion, the suspension system permits the position and orientation of the platform to change, relative to the base, in response to forces applied by the one or more teeth to the dental clamp, thereby accommodating changes in the position, orientation, and both of the one or more teeth by enabling corresponding changes in the position, orientation, or both of the platform, As also shown in FIG. 14, the method 1000 further comprises a step 1030 of rigidly clamping the dental clamp to the one or more teeth of the subject. As noted above, in respect of the examples of FIGS. 1-13, the dental clamp may clamp onto the one or more teeth by contacting and engaging with the one or more teeth of the subject directly. It is envisaged that the clamping is non-invasive, in the sense that the skin (e.g., of the gums) is not broken during the clamping and thus presents a minimal level of risk to the subject or patient. It should also be understood that, for convenience, step 1030 would typically be carried out after the robotic dental system has been provided in step 1010; however, this is of course not essential.

As further shown in FIG. 14, the method 1000 additionally comprises a step 1040 of introducing the distal end of the robotic arm into the mouth of the subject, using the one or more motors of the robotic arm. As shown in FIG. 14, step 1040 follows step 1010 and step 1030. In some examples, the introducing of the distal end of the robotic arm into the mouth of the subject is carried out under the control of the operator of the robotic dental system. For instance, the operator might provide a series of control inputs, such as via the user interface module 185, that progressively introduce the distal end of the robotic arm into the mouth of the subject. In such an example, after each control input, the robotic arm moves its distal end a small distance in a direction indicated by the operator's control input. In other examples, however, the introducing of the distal end of the robotic arm into the mouth of the subject could be carried out partly, or fully autonomously, for instance using sensors (e.g., proximity sensors, digital cameras, optical scanners, etc.) on the robotic arm to avoid colliding with the subject mouth and teeth and/or using a beacon, marker, fiducial or the like on the dental clamp for guidance.

FIG. 14 additionally shows an optional step 1020 of repositioning the platform of the treatment system to a location proximate the subject, using the suspension system. In this step, the operator may, for example, grasp a part of the treatment system, such as the platform or the robotic arm and thereby move the platform to a desired position proximate the subject. The location may, for example, provide improved access to the subject's mouth and/or the tooth/teeth to be treated, and/or may assist the operator in using the robotic dental system. In examples where the suspension system is an active suspension system (and hence comprises at least one motor), step 1020 may comprise operating the at least one motor of the suspension system, based on input from at least one force sensor, to move the platform to the location proximate the subject.

It should be appreciated that the robotic dental systems described herein may carry out various dental procedures. Because of their high level of accuracy, it is envisaged that the robotic dental systems described herein are particularly (but by no means exclusively) suitable for dental procedures that are carried out on the teeth themselves, as opposed to procedures carried out on, for example, the jawbone, where less accuracy is typically needed. In a specific example, the robotic dental systems may be configured (e.g. by suitable programming of processor(s) 181 and/or by storage of suitable instructions on computer-readable storage medium 182 and/or by the provision of a suitable end effector 140, such as a dental drill) so as to carry out tooth preparation in advance of the installation of a dental prosthetic, such as a crown or bridge. In another specific example, the dental systems may be configured (e.g., by suitable programming of processor(s) 181 and/or by storage of suitable instructions on computer-readable storage medium 182 and/or by the provision of a suitable end effector 140, such as a dental drill) to carry out removal of carious lesions of teeth.

Furthermore, while the above examples of robotic dental systems include only one robotic arm, it is envisaged that, in further examples two (or potentially more) robotic arms could be provided as part of the treatment system 110, rigidly coupled to the platform 111. In such examples, each robotic arm could be provided with a different end effector 140. In addition, or instead, the robotic dental system 100 could be configured (e.g., by suitable programming of the at least one processor 181 of the control system 180) such that the robotic arms (or a group of them) operate on a target tooth simultaneously or sequentially.

Still further, although in the above examples the dental clamp 150 is described as directly contacting and engaging with the one or more teeth of the subject 10, it is envisaged that, in other examples, the dental clamp 150 could additionally clamp onto other parts of the mouth of the subject 10 and/or could additionally clamp onto the jaw of the subject 10. Furthermore, in aspects of this disclosure that are different and/or broader than those exemplified above, the dental clamp could clamp onto the jaw of the subject 10 instead of the teeth of the subject 10. In still broader aspects, it is envisaged that a robotic surgical system could be provided that operates on a part of the body other than the teeth and that clamps onto that body part or an adjacent one, but that makes use of a platform and suspension system substantially similar to those described above.

Definitions

As used herein, the following terms shall have the following meanings, unless context indicates otherwise.

"Pressure" means a force applied perpendicular to a surface of an object per unit area over which the force is distributed. A non-zero pressure that is less than an ambient pressure, or less than a pressure in a reference location such as a suction material input port, is referred to as a "partial vacuum," but is nonetheless considered to be a pressure. Partial vacuum is measured in units of pressure, typically as a subtraction relative to ambient atmospheric pressure on Earth or the pressure in the reference location. "Gauge pressure" is pressure relative to an ambient, usually atmospheric, pressure, and a negative gauge pressure indicates a partial vacuum.

"Continually" means continuously or repeatedly, although not necessarily in perpetuity. The term continually encompasses periodically and occasionally. Continually generating a signal means generating a continuously varying signal over time or generating a series of (more than one) discrete signals over time. Continually generating a value, such as an error value, means generating a continuously varying value, such as an analog value represented by a continuously varying voltage, or generating a series of (more than one) discrete values over time, such as a series of digital or analog values.

While the present disclosure is described through the above-described exemplary embodiments, modifications to, and variations of, the illustrated embodiments may be made without departing from the concepts disclosed herein. For example, although specific parameter values, such as materials and dimensions, may be recited in relation to disclosed embodiments, within the scope of the invention, the values of all parameters may vary over wide ranges to suit different applications. Unless otherwise indicated in context or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

As used herein, including in the claims, an element described as being configured to perform an operation "or" another operation is met by an element that is configured to perform only one of the two operations. That is, the element need not be configured to operate in one mode in which the element performs one of the operations, and in another mode in which the element performs the other operation. The element may, however, but need not, be configured to perform more than one of the operations.

Although aspects of embodiments may be described with reference to flowcharts and/or block diagrams, functions, operations, decisions, etc. of all or a portion of each block, or a combination of blocks, may be combined, separated into separate operations or performed in other orders. References to a "module," "operation," "step" and similar terms are for convenience and not intended to limit their implementation. All or a portion of each block, module, operation, step or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The controller, etc. or portions thereof may be implemented by one or more suitable processors executing, or controlled by, instructions stored in a memory. Each processor may be a general-purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), non-volatile memory (NVM), non-volatile random-access memory (NVRAM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or infor- mation conveyed to a computer through a communication medium, including wired or wireless computer networks. Moreover, while embodiments may be described in connection with various illustrative data structures, database schemas and the like, systems may be embodied using a variety of data structures, schemas, etc.

Disclosed aspects, or portions thereof, may be combined in ways not listed herein and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective robot arm links, joints, etc. from one another and are not intended to indicate any particular order or total number of links or joints in any particular embodiment. Thus, for example, a given embodiment may include only a second link and a third joint.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the present disclosure described herein may be employed in practicing the present disclosure. It is intended that the following claims define the scope of the invention and that methods and structures within the scope of these claims and their equivalents be covered thereby.

What is claimed is:

1. A robotic dental system, comprising:
   a treatment system, which comprises:
      a dental clamp, which is configured to be rigidly clamped to one or more teeth of a subject;
      a robotic arm, a distal end of which is coupled to an end effector; and
      a platform, to which a proximal end of the robotic arm is coupled, the platform comprising a coupling portion configured to rigidly and releasably couple to the dental clamp, the platform and coupling portion being configured such that, when the dental clamp is rigidly coupled to the coupling portion, a rigid coupling between the dental clamp and the platform is thereby provided, so that a position and orientation of the platform remain fixed, relative to the dental clamp;
   a base; and
   a passive or active suspension system comprising a plurality of linkages and joints, wherein the suspension system mechanically couples the platform with the base, and supports a weight of the treatment system, and wherein, when the robotic dental system is operating in a treatment mode, with the dental clamp rigidly coupled to the coupling portion, the plurality of joints enable the linkages to move relative to one another so that the suspension system permits the position and orientation of the platform to change, relative to the base, in response to a force applied to the dental clamp, so as to accommodate changes in a position, orientation, and both of the dental clamp, through corresponding changes in the position, orientation or both of the platform, relative to the base, with the rigid coupling between the dental clamp and the platform causing the position and orientation of the platform to remain fixed, relative to the dental clamp, during such changes in the position, orientation or both of the platform relative to the base.

2. The robotic dental system of claim 1, wherein the suspension system is an active suspension system and comprises at least one motor.

3. The robotic dental system of claim 2, wherein, when the robotic dental system is operating in a treatment mode, the at least one motor is operated based on input from at least one force sensor so as to cause the position, orientation or both of the platform to change, relative to the base, in response to said forces applied to the dental clamp, thereby permitting corresponding changes in the position, orientation, or both of the dental clamp.

4. The robotic dental system of claim 2, wherein, when the robotic dental system is operating in a compliant mode, the at least one motor is operated, based on input from at least one force sensor, so as to cause the position, orientation or both of the platform to change, relative to the base, in response to forces applied to the treatment system by an operator of the robotic dental system, thereby permitting the operator to reposition the treatment system in a desired arrangement.

5. The robotic dental system of claim 1, wherein the suspension system is a passive suspension system, so that the suspension system permits external forces that are applied to the treatment system to mechanically cause the position and orientation of the platform to change.

6. The robotic dental system of claim 1, wherein the dental clamp is configured to be rigidly clamped to a plurality of teeth of the subject, and the robotic arm is operable to address at least two of the plurality of teeth.

7. The robotic dental system of claim 1, wherein the robotic arm is configured so as to be insertable into a mouth of the subject separately from the dental clamp.

8. The robotic dental system of claim 1, wherein the robotic dental system is configured to cause the robotic arm to perform a dental procedure on at least one target tooth.

9. The robotic dental system of claim 1, wherein the robotic arm has at least six degrees of freedom.

10. The robotic dental system of claim 1, wherein the robotic arm has more than six degrees of freedom.

11. The robotic dental system of claim 1, wherein the robotic arm comprises a plurality of robotic joints.

12. The robotic dental system of claim 1, wherein the robotic arm comprises at least four robotic joints.

13. The system of claim 1, wherein the end effector comprises a dental drill.

14. The system of claim 1, further comprising at least one processor, and a computer readable storage medium storing instructions that, when executed by the at least one processor, cause the system to perform the dental procedure.

15. The robotic dental system of claim 14, wherein the dental procedure is a tooth preparation procedure.

* * * * *